(12) United States Patent
Ben-Haim et al.

(10) Patent No.: US 6,892,091 B1
(45) Date of Patent: May 10, 2005

(54) CATHETER, METHOD AND APPARATUS FOR GENERATING AN ELECTRICAL MAP OF A CHAMBER OF THE HEART

(75) Inventors: Shlomo Ben-Haim, Haifa (IL); Joshua Porath, Haifa (IL); Frederick L. Herman, Zichron Yaacov (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/506,766

(22) Filed: Feb. 18, 2000

(51) Int. Cl.[7] .................................. A61B 5/0402
(52) U.S. Cl. ............................................ 600/509
(58) Field of Search ......................... 600/374, 393, 600/509, 512, 515; 607/115, 119, 122, 127

(56) References Cited

U.S. PATENT DOCUMENTS

| | | | |
|---|---|---|---|
| 4,649,924 A | 3/1987 | Taccardi | |
| 4,911,174 A | 3/1990 | Pederson et al. | |
| 5,265,602 A | 11/1993 | Anderson et al. | |
| 5,297,549 A | 3/1994 | Beatty et al. | 128/642 |
| 5,311,866 A * | 5/1994 | Kagan et al. | 128/642 |
| 5,331,966 A | 7/1994 | Bennett et al. | |
| 5,385,146 A * | 1/1995 | Goldreyer | 128/642 |
| 5,391,199 A | 2/1995 | Ben-Haim | 607/122 |
| 5,450,846 A | 9/1995 | Goldreyer | |
| 5,487,391 A | 1/1996 | Panescu | 128/699 |
| 5,546,951 A | 8/1996 | Ben-Haim | 128/702 |
| 5,553,611 A | 9/1996 | Budd et al. | 128/642 |
| 5,582,609 A | 12/1996 | Swanson et al. | 606/39 |
| 5,595,183 A | 1/1997 | Swanson et al. | 128/697 |
| 5,662,108 A | 9/1997 | Budd et al. | 128/642 |
| 5,676,153 A | 10/1997 | Smith et al. | |
| 5,718,241 A * | 2/1998 | Ben-Haim et al. | 128/702 |
| 5,738,096 A | 4/1998 | Ben-Haim | 128/653.1 |
| RE35,880 E | 8/1998 | Waldman et al. | 600/374 |
| 5,836,874 A | 11/1998 | Swanson et al. | 600/374 |
| 5,848,972 A | 12/1998 | Triedman et al. | 600/508 |
| 5,897,529 A | 4/1999 | Ponzi | 604/95 |
| 5,913,820 A | 6/1999 | Bladen et al. | 600/407 |

(Continued)

FOREIGN PATENT DOCUMENTS

| | | |
|---|---|---|
| EP | 0499491 A | 8/1992 |
| EP | 0 661 948 B1 | 11/1997 |

(Continued)

OTHER PUBLICATIONS

Communication dated Apr. 19, 2004 from the EPO regarding European Patent Application No. 01301387.5 (attached).

(Continued)

*Primary Examiner*—Jeffrey R. Jastrzab
*Assistant Examiner*—Frances P. Oropeza
(74) *Attorney, Agent, or Firm*—Louis J. Capezzuto

(57) ABSTRACT

A novel apparatus and method for rapidly generating an electrical map of a chamber of a heart utilizes a catheter including a body having a proximal end and a distal end. The distal end has a distal tip and an array of non-contact electrodes having a proximal end and a distal end and at least one location sensor. Preferably, two location sensors are utilized. The first location sensor is preferably proximate to the catheter distal tip and the second location sensor is preferably proximate to the proximal end of the non-contact electrode array. The catheter distal end further preferably includes a contact electrode at its distal tip. Preferably, at least one and preferably both of the location sensors provide six degrees of location information. The location sensor is preferably an electromagnetic location sensor. The catheter is used for rapidly generating an electrical map of the heart within at least one cardiac cycle and preferably includes cardiac ablation and post-ablation validation.

41 Claims, 7 Drawing Sheets

U.S. PATENT DOCUMENTS

| | | | | |
|---|---|---|---|---|
| 5,938,602 A | * | 8/1999 | Lloyd | 600/424 |
| 5,938,603 A | | 8/1999 | Ponzi | 600/424 |
| 5,964,757 A | | 10/1999 | Ponzi | 606/45 |
| 6,104,944 A | * | 8/2000 | Martinelli | 600/424 |
| 6,171,306 B1 | * | 1/2001 | Swanson et al. | 606/41 |
| 6,272,371 B1 | * | 8/2001 | Shomo | 600/424 |

FOREIGN PATENT DOCUMENTS

| | | | |
|---|---|---|---|
| EP | 0911059 A2 | 10/1998 | |
| EP | 0 900 547 A1 | 3/1999 | |
| EP | 0 900 548 A1 | 3/1999 | |
| EP | 0911059 A | 4/1999 | |
| WO | WO 92/21278 A1 | 12/1992 | |
| WO | WO 96/05768 | 2/1996 | |
| WO | 96/05768 * | 2/1996 | A61B/5/06 |
| WO | WO 97/25917 | 7/1997 | |
| WO | WO 98/29032 A1 | 7/1998 | |
| WO | WO 98/43530 | 10/1998 | |
| WO | WO 99/06112 | 2/1999 | |

OTHER PUBLICATIONS

Liu, Zhiwei W.; Jia, Ping; Biblo, Lee A.; Taccardi, Bruno; and Rudy, Yoram; Endocardial Potential Mapping from a Noncontact Nonexpandable Catheter: A Feasibility Study; Annals of Biomedical Engineering, vol. 26, 1998, pp 994–1009.

Michael Kass, Andrew Witkin and Demetri Terzopoulos; Snakes: Active Contour Models; Proceedings of First International Conference Vision, 1987 pp 257–268.

Demetri Terzopoulos; Regularization of Inverse Visual Problems Involving Discontinuities; IEEE Transactions on Pattern Analysis and Machine Intelligence, vol. PAMI–8, No. 4, Jul. 1986 pp. 413–424.

Kok F. Lai and Roland T. Chin; Deformable Contours: Modeling and Extraction; IEEE Transactions on Pattern Analysis and Machine Intelligence, vol. 17, No. 11, pp 1084–1090.

D. Onnasch, P.H. Heintzen; A Versatile Program for the Documentation and Comparison of Traced Heart Contours; Computers in Cardiology, Long Beach California, IEEE Computer Society, 1975, pp 257–262.

Richard O. Duda and Peter E. Hart; Use of the Hough Transformation To Detect Lines and Curves in Pictures; Graphics and Image Proceeding; Communications of the ACM; Jan. 1972 vol. 15 No. 1 pp 11–15.

European Patent Office Search Report, dated Jun. 12, 2002 for EPO Appln. No. EP 02251741 which relates to U.S. Appl. No. 09/805,903, filed Mar. 13, 2001.

Partial European Search Report, dated Jul. 23, 2002 for EPO Appln. No. EP 01301387.

* cited by examiner

CATHETER, METHOD AND APPARATUS FOR GENERATING AN ELECTRICAL MAP OF A CHAMBER OF THE HEART

FIELD OF THE INVENTION

The invention is directed to methods, apparatus and associated catheters for rapidly generating an electrical map of a chamber of a heart utilizing an array of non-contact electrodes for obtaining information indicative of chamber electrical activity, and optionally, of chamber geometry.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

Commonly assigned U.S. Pat. No. 5,546,951; U.S. patent application Ser. No. 08/793,371; and PCT application WO 96/05768, which are incorporated herein in their entirety by reference, disclose methods for sensing an electrical property of heart tissue, for example, local activation time, as a function of the precise location within the heart. The data are acquired with one or more catheters that are advanced into the heart using catheters that have electrical and location sensors in their distal tips. Methods of creating a map of the electrical activity of the heart based on these data are disclosed in commonly assigned U.S. patent applications Ser. Nos. 09/122,137 and 09/357,559 filed on Jul. 24, 1998 and Jul. 22, 1999, respectively, which are also incorporated herein in their entirety by reference. As indicated in these applications, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096 which is incorporated herein in its entirety by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole.

Accordingly, multiple-electrode catheters have been developed to simultaneously measure electrical activity at multiple points in the heart chamber.

Two approaches have been previously taken to acquire cardiac data using multi-electrode catheters by contact and non-contact methods.

U.S. Pat. No. 5,487,391, directed to systems and methods for deriving and displaying the propagation velocities of electrical events in the heart, is illustrative of contact methods found in the art. In the system disclosed in the '391 patent, the electrical probe is a three-dimensional structure that takes the form of a basket. In the illustrated embodiment, the basket is composed of 8 splines, each of which carries eight electrodes, for a total of 64 electrodes in the probe. The basket structure is designed such that when deployed, its electrodes are held in intimate contact against the endocardial surface. A problem with the catheters disclosed in the '391 patent is that they are both difficult and expensive to produce. The large number of electrodes in such catheters is also very demanding of the data recording and processing subsystem. There are additional complexities associated with the deployment and withdrawal of these catheters, and increased danger of coagulation.

U.S. Pat. No. 5,848,972 to Triedman et al. discloses a method for endocardial activation mapping using a multi-electrode catheter. In the method of the '972 patent, a multi-electrode catheter, preferably, a 50-electrode Webster-Jenkins™ basket catheter from Cordis-Webster of Baldwin Park, Calif., is advanced into a chamber of the heart. Anteroposterior (AP) and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG. Interestingly, Triedman et al. differentiate between those electrodes that register electrical activity and those that do not due to absence of close proximity to the endocardial wall. After the initial electrograms are recorded, the catheter is repositioned, and fluorograms and electrograms are once again recorded. An electrical map is then constructed from the above information.

U.S. Pat. No. 4,649,924 to Taccardi discloses a method for the detection of intracardiac electrical potential fields. The '924 patent is illustrative of the non-contact methods that have been proposed to simultaneously acquire a large amount of cardiac electrical information. In the method of the '924 patent, a catheter having a distal end portion is provided with a series of sensor electrodes distributed over its surface and connected to insulated electrical conductors for connection to signal sensing and processing means. The size and shape of the end portion are such that the electrodes are spaced substantially away from the wall of the cardiac chamber. The method of the '924 patent is said to detect the intracardiac potential fields in only a single cardiac beat. The sensor electrodes are preferably distributed on a series of circumferences lying in planes spaced from each other. These planes are perpendicular to the major axis of the end portion of the catheter. At least two additional electrodes are provided adjacent the ends of the major axis of the end portion. The '924 patent discloses only a single exemplary embodiment in which the catheter comprises four circumferences with eight electrodes spaced equiangularly on each circumference. Thus, in that exemplary embodiment, the catheter comprises at least 34 electrodes (32 circumferential and 2 end electrodes).

PCT application WO 99/06112 to Rudy (the "Rudy method"), the disclosure of which is incorporated herein by reference discloses an electrophysiological cardiac mapping system and method based on a non-contact, non-expanded multi-electrode catheter. Electrograms are obtained with catheters having from 42 to 122 electrodes. In addition to the above-described problem of complexity of multi-electrode catheters, the Rudy method requires prior knowledge of the relative geometry of the probe and the endocardium, which must be obtained via an independent imaging modality such as transesophogeal echocardiography. In the Rudy method, after the independent imaging, non-contact electrodes are used to measure cardiac surface potentials and construct maps therefrom. Briefly, the Rudy method involves the following steps (after the independent imaging step): (a) measuring electrical potentials with a plurality of electrodes disposed on a probe positioned in the heart; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients.

U.S. Pat. No. 5,297,549 to Beatty et al. (the "Beatty method"), the disclosure of which is incorporated herein by reference, discloses a method and apparatus for mapping the electrical potential distribution of a heart chamber. In the Beatty method, an intra-cardiac multielectrode mapping catheter assembly is inserted into the heart. The mapping catheter assembly includes a multi-electrode array with an integral reference electrode, or, preferably, a companion reference catheter. In use, the electrodes are deployed in the form of a substantially spherical array. The electrode array is spatially referenced to a point on the endocardial surface by the reference electrode or by the reference catheter which is brought into contact with the endocardial surface. The preferred electrode array catheter is said to carry at least 24 individual electrode sites. Additionally, the Beatty method requires knowledge of the location of each of the electrode sites on the array, as well as a knowledge of the cardiac geometry. These locations are preferably determined by the method of impedance plethysmography.

U.S. Pat. No. 5,311,866 to Kagan et al. discloses a heart mapping catheter assembly including an electrode array defining a number of electrode sites. The mapping catheter assembly also comprises a lumen to accept a reference catheter having a distal tip electrode assembly which may be used to probe the heart wall. In the preferred construction, the mapping catheter comprises a braid of insulated wires, preferably having 24 to 64 wires in the braid, each of which are used to form electrode sites. The catheter is said to be readily positionable in a heart to be used to acquire electrical activity information from a first set of non-contact electrode sites and/or a second set of in-contact electrode sites.

U.S. Pat. Nos. 5,385,146 and 5,450,846 to Goldreyer disclose a catheter that is said to be useful for mapping electrophysiological activity within the heart. The catheter body has a distal tip which is adapted for delivery of a stimulating pulse for pacing the heart or an ablative electrode for ablating tissue in contact with the tip. The catheter further comprises at least one pair of orthogonal electrodes to generate a difference signal indicative of the local cardiac electrical activity adjacent the orthogonal electrodes.

U.S. Pat. No. 5,662,108 to Budd et al. discloses a process for measuring electrophysiologic data in a heart chamber. The method involves, in part, positioning a set of active and passive electrodes into the heart; supplying current to the active electrodes, thereby generating an electric field in the heart chamber; and measuring said electric field at said passive electrode sites. In one of the disclosed embodiments, the passive electrodes are contained in an array positioned on an inflatable balloon of a balloon catheter. In preferred embodiments, the array is said to have from 60 to 64 electrodes.

In summary, a number of methods have been proposed for increasing the speed of acquiring an electrical map of the heart. In general, these methods suffer from requiring complex equipment, or often require external imaging modalities for acquiring positional information. Moreover, these prior art systems are known to produce maps with limited accuracy. Accordingly, there is a need for equipment and methods that overcome these prior art limitations.

SUMMARY OF THE INVENTION

The present invention is a novel system/apparatus and method for rapidly generating a map of a characteristic of an organ, such as a chamber of the heart, within a defined period of time. One aspect of the invention is directed to a catheter for use with the system for generating an electrical map of the heart. The catheter includes a body having a proximal end and a distal end. The distal end has a distal tip and comprises a contact electrode at its distal tip and an array of non-contact electrodes having a proximal end and a distal end, and at least one location sensor.

In the case of a catheter having only a single location sensor, the sensor is preferably proximate the catheter distal tip. More preferably, the catheter comprises first and second location sensors. The first location sensor is preferably proximate the catheter distal tip and the second location sensor is proximate the proximal end of the non-contact electrode array. At least one and preferably both of the sensors used in the catheter of the invention provides six degrees of location information. The location sensor used in the catheter of the invention is preferably an electromagnetic location sensor.

The distal tip electrode used in the catheter of the invention is preferably a bipolar electrode. The array of non-contact electrodes preferably comprises from about 12 to about 32 electrodes, and more preferably between about 16 to about 24 electrodes. In one preferred embodiment, the non-contact electrode array in the catheter of the invention comprises less than about 20 electrodes.

In another embodiment, the invention is directed to a catheter for generating an electrical map of the heart in which the catheter has a body having a proximal end and a distal end. The distal end comprises a distal tip and an array of non-contact electrodes having a distal end and a proximal end, as well as at least one location sensor proximate to the catheter distal tip.

Another aspect of the invention is directed to a method for rapidly generating an electrical map of the heart that depicts an electrical characteristic of the chamber as a function of chamber geometry. The method of the invention comprises the steps of providing a catheter including a body having a proximal end a distal end. The distal end comprises a distal tip and a contact electrode at its distal tip, an array of non-contact electrodes having a distal end and a proximal end, and at least one location sensor. The catheter is advanced into the chamber of the heart and the wall of the chamber of the heart is contacted with the contact electrode at a plurality of contact points. Electrical information and location information are acquired from each of the electrodes and location sensors, respectively. The acquisition of electrical and location information takes place over at least one cardiac cycle while the contact electrode is in contact with each of the contact points. An electrical map of the heart chamber is generated from the acquired location and electrical information.

In practicing the method of the invention with a catheter having only a single location sensor, the sensor is preferably proximate to the catheter distal tip. More preferably, the method of the invention is carried out with a catheter comprising first and second location sensors. The first location sensor is preferably proximate the catheter distal tip and the second location sensor is proximate the proximal end of the non-contact electrode array. Preferably, at least one and more preferably both of the catheter sensors used in the process of the invention provide six degrees of location information. The location sensor used in the catheter of the invention is preferably an electromagnetic location sensor.

The distal tip electrode of the catheter used in practicing the method of the invention is preferably a bipolar electrode. The array of non-contact electrodes preferably comprises from about twelve to about thirty-two electrodes, and more preferably between about sixteen to about twenty-four electrodes. In one preferred embodiment, the non-contact electrode array in the catheter of the invention comprises less than about twenty electrodes.

In the method of the invention, the contacting step is preferably effected at at least about five contact points, and more preferably, at between about five to about fifteen contact points.

The electrical map generated by the method of the invention depicts an electrical characteristic of the heart chamber such as voltage, impedance, conduction velocity or local activation time as a function of chamber geometry. The location information used to generate the electrical map comprises the location of the contact electrode at each of the contact points, and, preferably, further comprises the location of each of the non-contact electrodes during data acquisition.

The electrical information acquired during the data acquisition step is preferably the voltage at each of the electrodes. The electrical information at each of the contact points is measured by the contact electrode. In one preferred embodiment, the electrical characteristics intermediate the contact points are derived from data measured by the contact electrodes, preferably in combination with measurements by the non-contact electrodes.

The resultant electrical map of the heart chamber generated by the method of the invention preferably depicts the geometry of the heart at a single point in the heart cycle, preferably, at end-diastole. The map is preferably output to a display device such as a computer display or a computer printer.

In an alternative embodiment, the method of the invention comprises the steps of providing a catheter including a body having a proximal end and a distal end. The distal end comprises a distal tip, an array of non-contact electrodes having a distal end and a proximal end, and at least one location sensor. The catheter is advanced into the chamber of the heart and the wall of the chamber of the heart is contacted with the catheter distal tip at a plurality of contact points. Electrical information and location information is acquired from each of the electrodes and location sensors, respectively, over at least one cardiac cycle while the catheter distal tip is in contact with each of the contact points. An electrical map of the heart chamber is generated from the acquired location and electrical information.

Another aspect of the invention is directed to a novel apparatus for rapidly generating an electrical map of a chamber of a heart wherein the map depicts an electrical characteristic of the chamber as a function of chamber geometry. The apparatus of the invention comprises a catheter including a body having a proximal end and a distal end. The distal end of the catheter comprises a distal tip, a contact electrode at its distal tip, an array of non-contact electrodes having a distal end and a proximal end, and at least one location sensor. The catheter is adapted to contacting the wall of the chamber of the heart with the contact electrode at a plurality of contact points. A signal processor is used for acquiring electrical information and location information from each of the electrodes and location sensors, respectively, over at least one cardiac cycle while said contact electrode is in contact with each of the contact points. The signal processor is also used for computing an electrical map of the heart chamber from the acquired location and electrical information.

In an alternative embodiment, the apparatus of the invention comprises a catheter including a body having a proximal end and a distal end. The distal end comprises a distal tip, an array of non-contact electrodes having a proximal end and a distal end, and at least one location sensor. The catheter is adapted to contacting the wall of the chamber of the heart with the catheter distal tip at a plurality of contact points. A signal processor is used for acquiring electrical information and location information from each of the electrodes and location sensors, respectively, over at least one cardiac cycle while said catheter distal tip is in contact with each of the contact points. The signal processor is also used for computing an electrical map of the heart chamber from the acquired location and electrical information.

Preferably, the catheter in the apparatus of the invention comprises first and second location sensors. The first location sensor is proximate to the catheter distal tip and the second location sensor is proximate to the proximal end of the electrode array. At least one of the location sensors used in the apparatus of the invention is preferably an electromagnetic location sensor. The apparatus preferably further comprises means for displaying the geometric and electrical maps.

Another aspect of the invention also includes ablating a region of a chamber of a heart based on the generated map.

The method of the invention preferably further comprises validating the effectiveness of the ablation procedure, preferably, by acquiring additional electrical information from the catheter following the ablation procedure.

It is an object of the invention to provide a catheter, method and apparatus for generating an electrical map of a chamber of a heart more rapidly than using single contact electrode catheters used in the prior art.

It is another object of the invention to provide a catheter, method and apparatus for generating an electrical map of a chamber of a heart using both contact and non-contact electrodes.

It is another object of the invention to provide a catheter, method and apparatus for generating an electrical map of a chamber of the heart that is more accurate than prior art maps generated using only non-contact electrodes.

It is another object of the invention to provide a catheter, method and apparatus that may be used to simultaneously acquire location as well as contact and non-contact electrical information in a chamber of a heart.

It is another object of the invention to provide a catheter, method and apparatus for generating an electrical map of a chamber of a heart without the need to use external imaging modalities.

It is another object of the invention to provide a catheter and methods for ablating a region of the heart, with the capability of rapidly validating the effectiveness of the ablation procedure by collecting additional post-ablation electrical information.

These and other objects, features and advantages of the present invention will be more readily apparent from the detailed description set forth below, taken in conjunction with the accompanying drawings.

DETAILED DESCRIPTION OF THE PREFERRED EMBODIMENTS

The present invention is a novel apparatus (system), including its associated catheter as well as novel method for conducting a rapid or fast mapping procedure in an organ such as the chamber of a heart. The present invention is directed to conducting this rapid mapping procedure, usually based on electrical activity through the heart tissue, within a minimum period of time.

Figure 1:
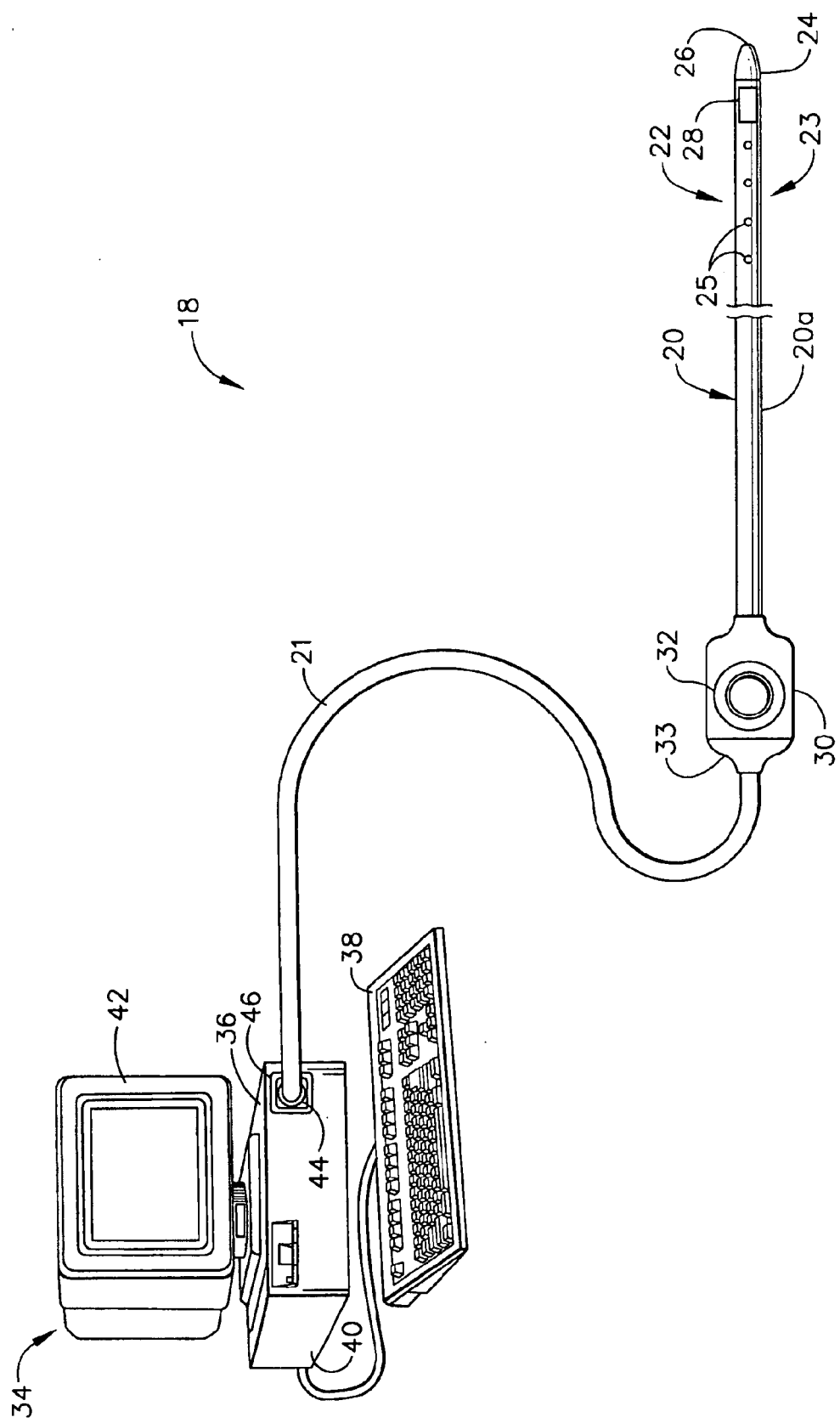
FIG. 1 is a schematic drawing of selected elements of a system employing the catheter of the invention.
Figure 2:
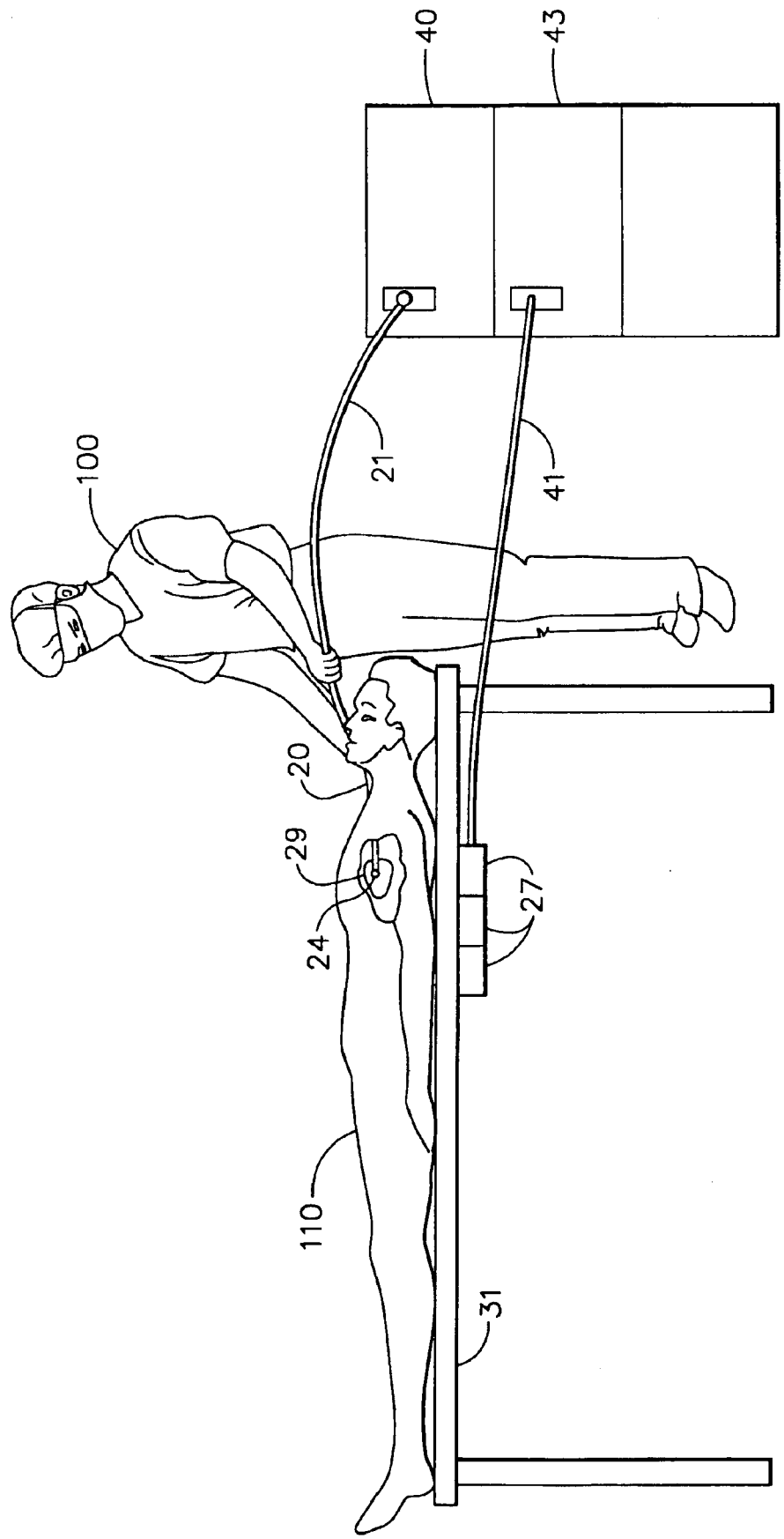
FIG. 2 shows additional elements of a system employing the catheter of the invention.
Figure 7A:
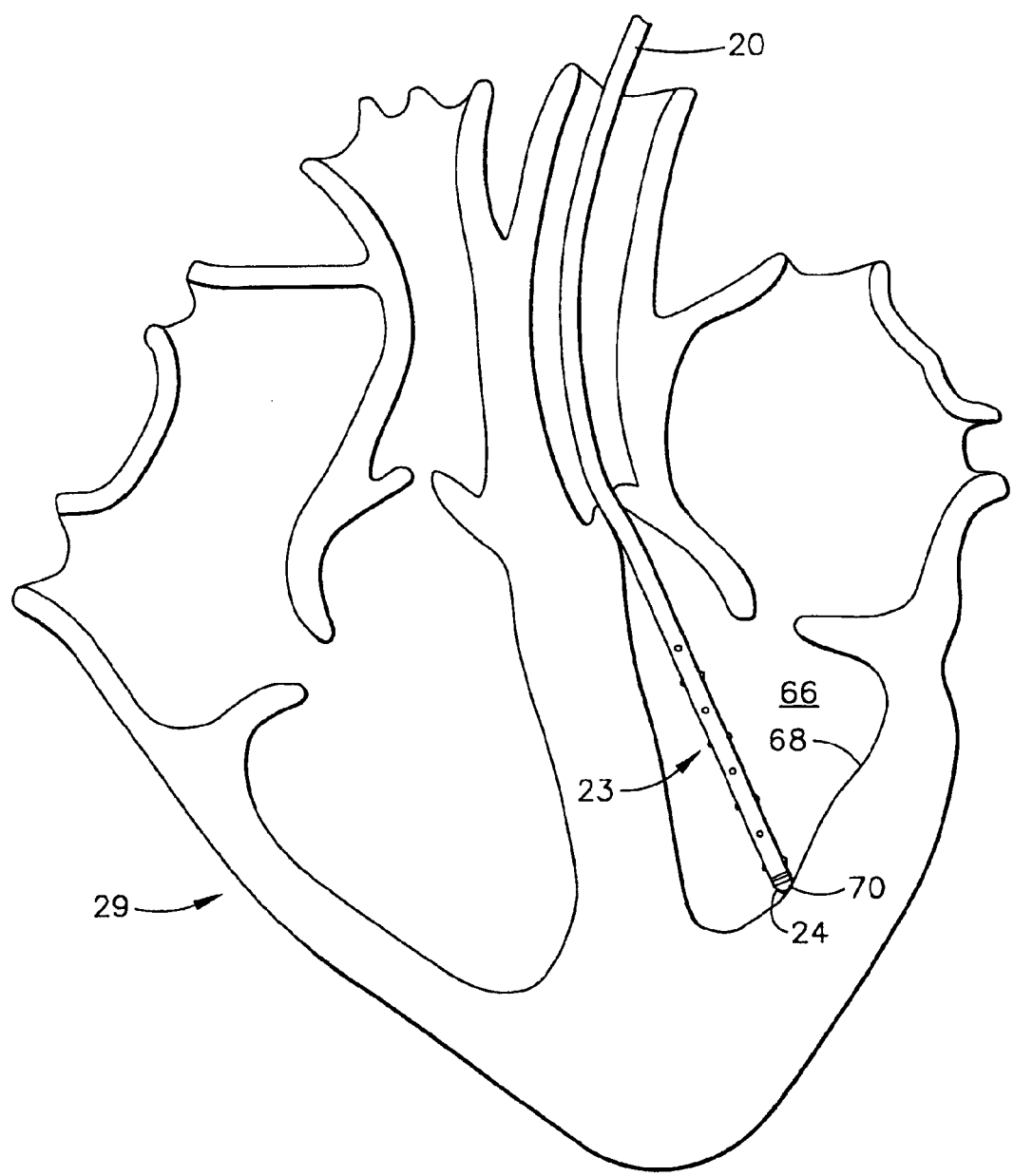
FIG. 7A depicts the distal end of the catheter of FIG. 3B in contact with a first contact point within the left ventricle of a heart.
Figure 7B:
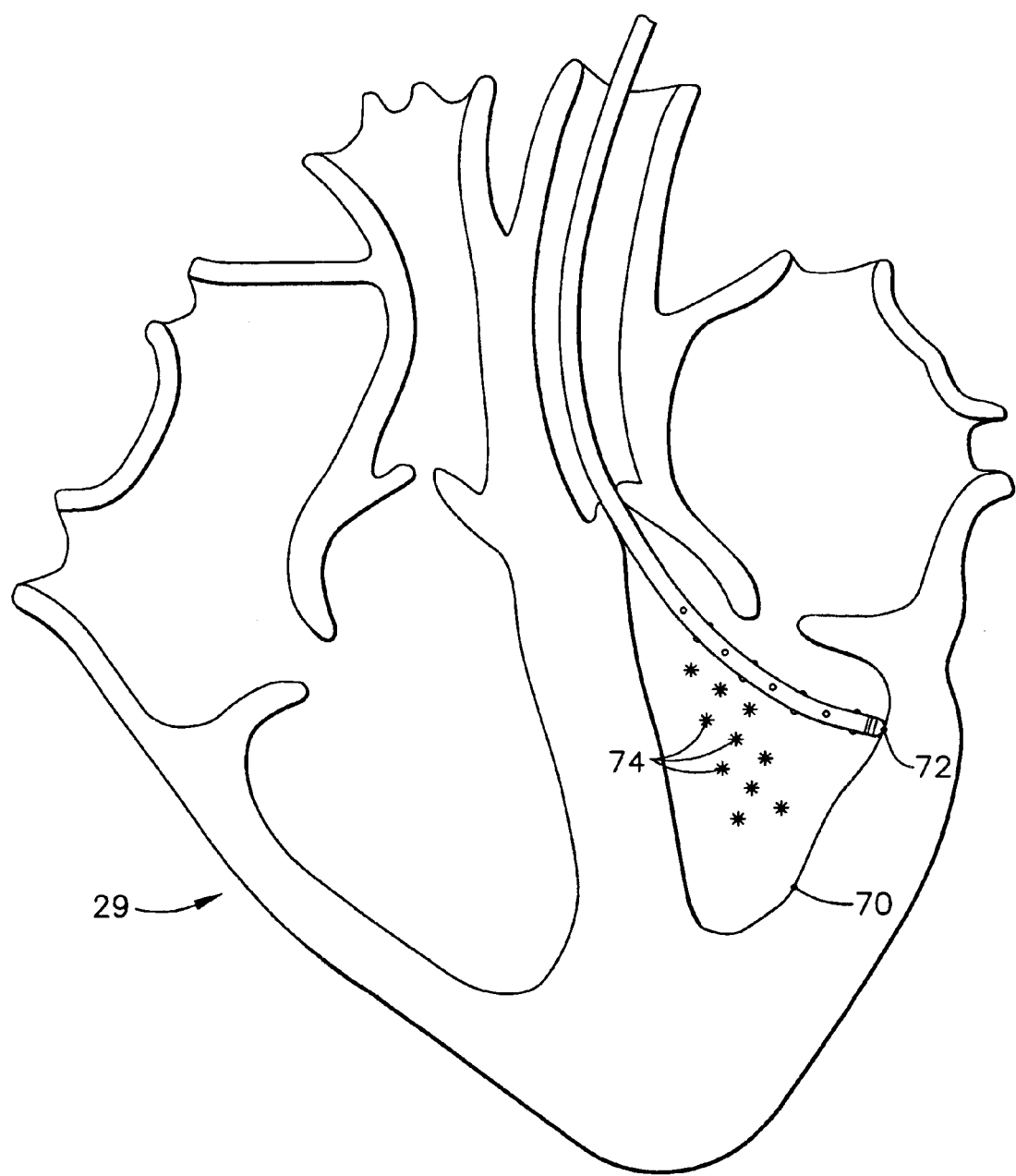
FIG. 7B depicts the distal end of the catheter of FIG. 3B in contact with a second contact point within the left ventricle of a heart.

The present invention includes a novel rapid diagnostic mapping and therapeutic delivery system, generally designated 18, as best shown in FIG. 1, comprising a novel fast diagnostic mapping and therapeutic delivery catheter 20 for insertion into the human body, and preferably, into a chamber 56 and 66 (FIGS. 5 and 7A) of a human heart 29 (FIGS. 2, 7A and 7B). The catheter 20 includes a catheter body 20a having a distal end 22. The distal end 22 includes an electrode 24 at distal tip 26 for measuring the electrical properties of the heart tissue. Electrode 24 is also useful for sending electrical signals to the heart for diagnostic purposes, e.g., for pace mapping, and/or for therapeutic purposes, e.g., for ablating defective cardiac tissue. Distal end 22 of catheter 20 further includes an array 23 of non-contact electrodes 25 for measuring far field electrical signals in the heart chamber. The array 23 of non-contact electrodes 25 is a linear array in that the non-contact electrodes 25 are linearly arranged along the longitudinal axis 47 (FIG. 3A) of the catheter distal end 22. Distal end 22 of catheter 20 further includes at least one location sensor 28 that generates signals used to determine the position and orientation of the catheter within the body. Location sensor 28 is preferably adjacent to distal tip 26 of catheter 20. There is preferably a fixed positional and orientational relationship of location sensor 28, tip 26 and electrode 24.

Catheter 20 preferably includes a handle 30, which includes controls 32 to steer the distal end 22 of the catheter 20 in a desired direction, such as deflecting the distal end 22, or to position and/or orient it as desired.

The system 18 as shown in FIG. 1 further comprises a console 34, which enables the user to observe and regulate the functions of catheter 20. Console 34 preferably includes a computer 36 (as a signal processor), keyboard 38, signal processing circuits 40 which are typically inside the computer, and display 42. Signal processing circuits 40 typically receive, amplify, filter and digitize signals from catheter 20, including signals generated by location sensor 28, tip electrode 24 and non-contact electrodes 25 whereupon these digitized signals are received and used by computer 36 to compute the position and orientation of the catheter as well as the electrical characteristics of the heart chamber. Alternatively, appropriate circuitry may be associated with the catheter 20 itself so that circuits 40 receive signals that are already amplified, filtered and/or digitized.

Catheter 20 is coupled to computer 36 via an extension cable 21, which at its proximal end comprises a connector 44 adapted to fit in a mating receptacle 46 on console 34. The distal end of cable 21 comprises a receptacle 33 which connects to catheter handle 30. Receptacle 33 is preferably configured to receive catheters of a specific model, and preferably includes user-evident identification of the specific model. One of the advantages in using cable 21 is the ability to connect different models and types of catheters, such as those catheters having different handle configurations, to the same console 34. Different cables 21 can be used to connect a large variety of catheters to console 34. Another advantage in having a separate cable 21 is in the fact that the cable 21 does not come into contact with patients and therefore it is possible to re-use the cable 21 without sterilization.

Cable 21 further contains one or more isolation transformers (not shown in the figures), which electrically isolate catheter 20 from console 34. The isolation transformers are preferably contained in receptacle 33. Alternatively, isolation transformers may be contained in the associated system electronics.

Additional components used in system 18 with catheter 20 of the present invention are illustrated schematically in FIG. 2. A physician 100 inserts catheter 20 through an incision in the vasculature, e.g., using an intravascular approach, into a chamber 56 and 66 (FIGS. 5, 7A and 7B) of a heart 29 of a patient 110, so that distal tip electrode 24, array 23 of non-contact electrodes 25 and location sensor 28 are inside the chamber. In accordance with an exemplary location sensor described in PCT patent application number WO 96/05768, filed Jan. 24, 1995, and U.S. Pat. No. 5,391,199, which are assigned to the assignee of the present application and whose disclosures are incorporated herein by reference, sensor 28 generates signals in response to externally applied magnetic fields generated by electromagnetic field generator coils 27 which are located near the patient 110 such as fixed to operating table 31. The magnitude of the signals generated by sensor 28 depends on the position and orientation of the sensor in the applied magnetic field. Field generator coils 27 are connected via cable 41 to driver circuits 43. Circuits 43 are connected to computer 36 (FIG. 1), which controls the operation of the generating coils. Alternatively, the system of the invention may employ field generator coils in the catheter and sensors external to the patient.

While the catheter, process and apparatus of the invention are described herein with reference to electromagnetic sensors, any other location sensor that provides three-dimensional position information and, optionally, orientation information, may be used in the practice of the invention. Illustrative sensors that are also useful include acoustic sensors and magnetic sensors.

Preferably, measurements by location sensor 28 are substantially synchronized with the heart cycle, so that the resultant maps of electrical activity of the heart chamber 56 and 66 depict the chamber geometry at a single point in the heart cycle. Preferably, the maps depict the heart 29 at the end-diastole point in the heart cycle. Synchronization of the locations to a point in the cardiac cycle eliminates errors that may otherwise arise in determining positions of contact electrode 24 and non-contact electrodes 25 due to movement of the heart 29.

Figure 3C:
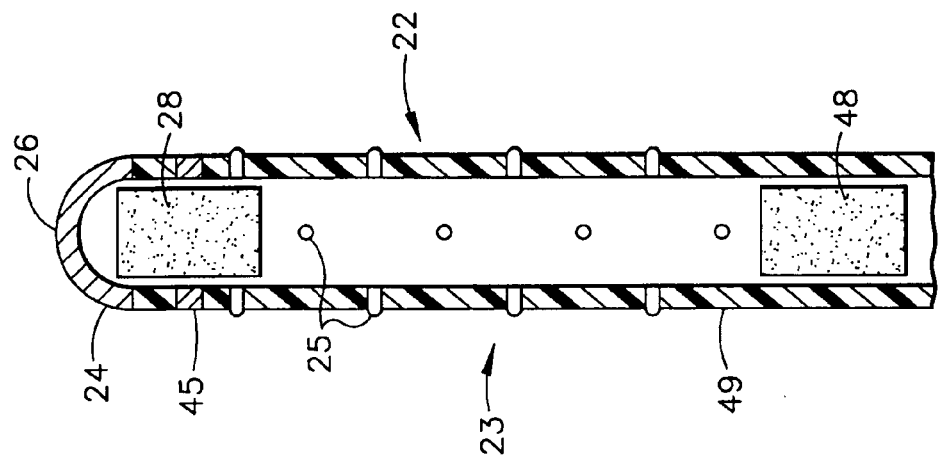
FIG. 3C shows a partial cross-sectional view of the catheter of FIG. 3B.
Figure 3B:
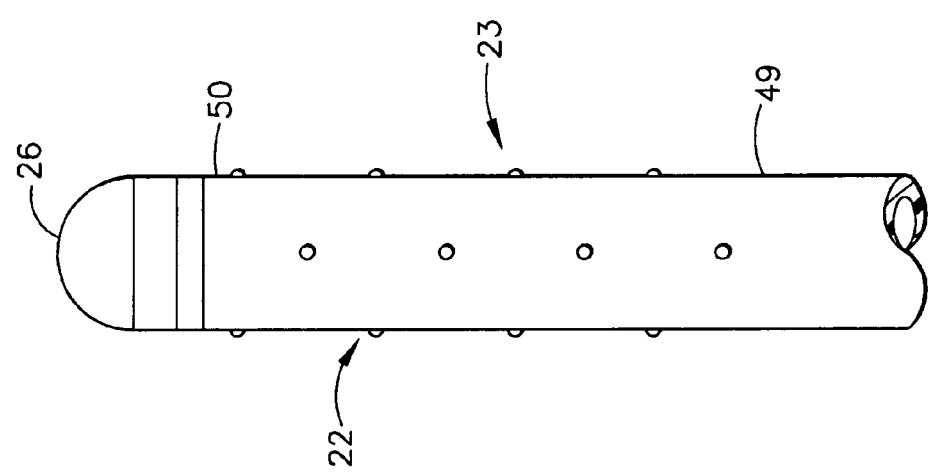
FIG. 3B shows the catheter of FIG. 3A rotated by 90° about its longitudinal axis.
Figure 3A:
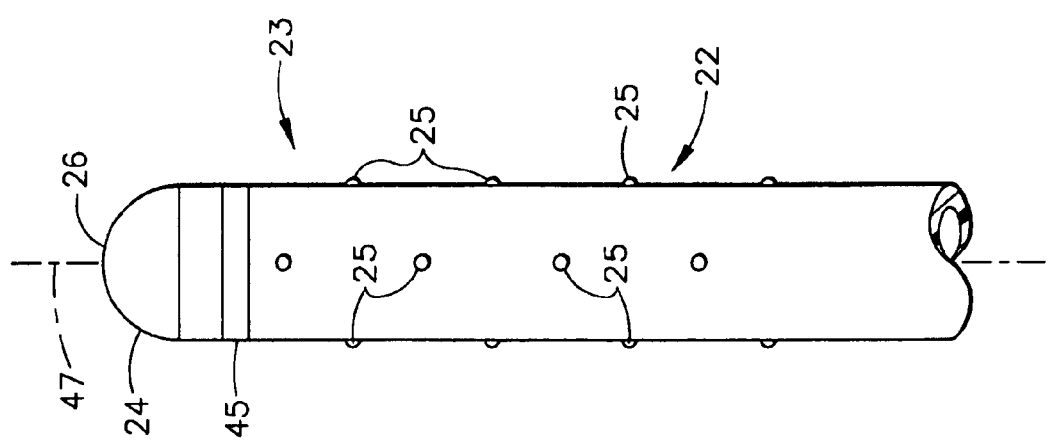
FIG. 3A shows a front plan view of one embodiment of the catheter of the invention.

FIG. 3A is a plan view of the distal end of one preferred embodiment of the catheter of the invention. FIG. 3B depicts the catheter of FIG. 3A rotated by 90° about its longitudinal axis 47. FIG. 3C depicts the catheter of FIG. 3B in cross-section along line 3B—3B. As shown in FIG. 3A, the catheter comprises tip electrode 24 and ring electrode 45. Together, these two electrodes function as a bipolar contact electrode. The array 23 of non-contact electrodes 25 has a proximal end 49 and a distal end 50. Array 23 consists of a plurality of electrodes 25, for instance, sixteen point electrodes 25. Each electrode 25 is circular in cross-section and has a diameter of 1 mm. The electrodes 25 in array 23 are arranged in four columns spaced circumferentially around the catheter distal end 22 in 90° increments. The location of the electrodes 25 in each column is longitudinally offset relative to the location of the corresponding electrodes in adjacent columns. This arrangement of non-contact electrodes 25 in array 23 allows the non-contact electrodes 25 to simultaneously receive far-field electrical signals from all walls of the chamber 56 and 66 in which the catheter 20 is advanced. The catheter 20 further comprises two location sensors 28 and 48 wherein sensor 28 is at the catheter distal tip and sensor 48 is near the proximal end 49 of array 23. Not shown in FIG. 3C are wires that connect each of the sensors 28 and 48 and each of the electrodes 24, 25 and 45 to handle 30, from which signals are transmitted to circuits 40. Likewise not shown is a deflection mechanism which permits deflection of the catheter tip via control 32 on catheter handle 30. The specific design of the catheter deflection mechanism is not critical to the invention, and may be any of the designs for catheter deflection mechanisms known in the art. Catheter steering/deflection mechanisms are disclosed, for example, in U.S. Pat. Nos. 5,964,757; 5,897,529; and 5,938,603; in EP Patent Applications EP 0900547 and EP 0900548, and in PCT Patent Application WO 98/43530, the disclosures of which are hereby incorporated in their entirety by reference.

Figure 4:
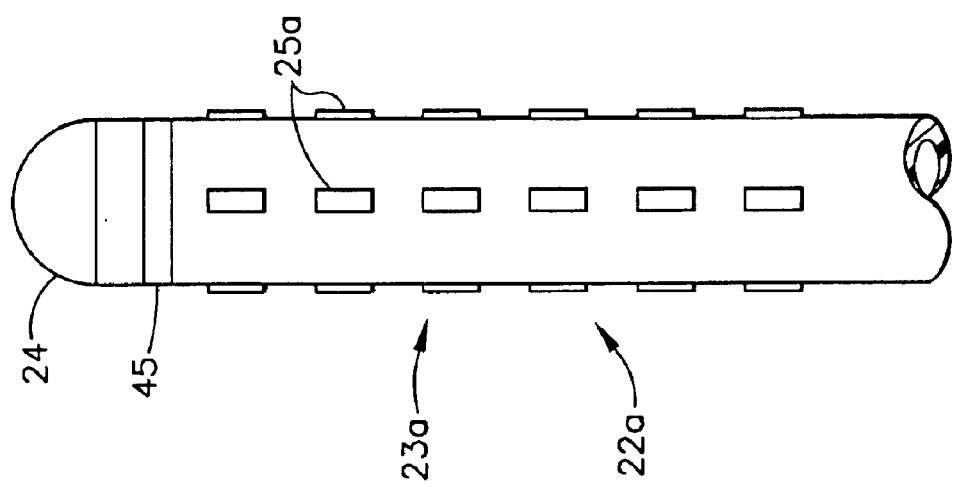
FIG. 4 shows a view of another preferred embodiment of the catheter of the invention.

FIG. 4 shows an alternate embodiment distal end 22a for the catheter 20 of the invention. The catheter 20 consists of tip electrode 24 and ring electrode 45. An array 23a of non-contact electrodes 25a consists of a total of twenty-four non-contact electrodes 25a arranged in four columns of six electrodes each and spaced circumferentially at 90° increments about the catheter distal end 22a. In the embodiment shown in FIG. 4, the non-contact electrodes 25a are rectangular in shape, having dimensions of 1 mm×3 mm, and are spaced within a column at a distance of 8 mm between centers. The catheter distal end 22a of FIG. 4 likewise contains two location sensors (not shown), one at the catheter tip 24 and the other at the proximal end of electrode array 23a.

Electrode array 23a preferably comprises from about twelve to about thirty-two non-contact electrodes 25a. More preferably, array 23a comprises from about sixteen to about twenty-four non-contact electrodes 25a. In one preferred embodiment, array 23a comprises less than twenty non-contact electrodes 25a.

Figure 5:
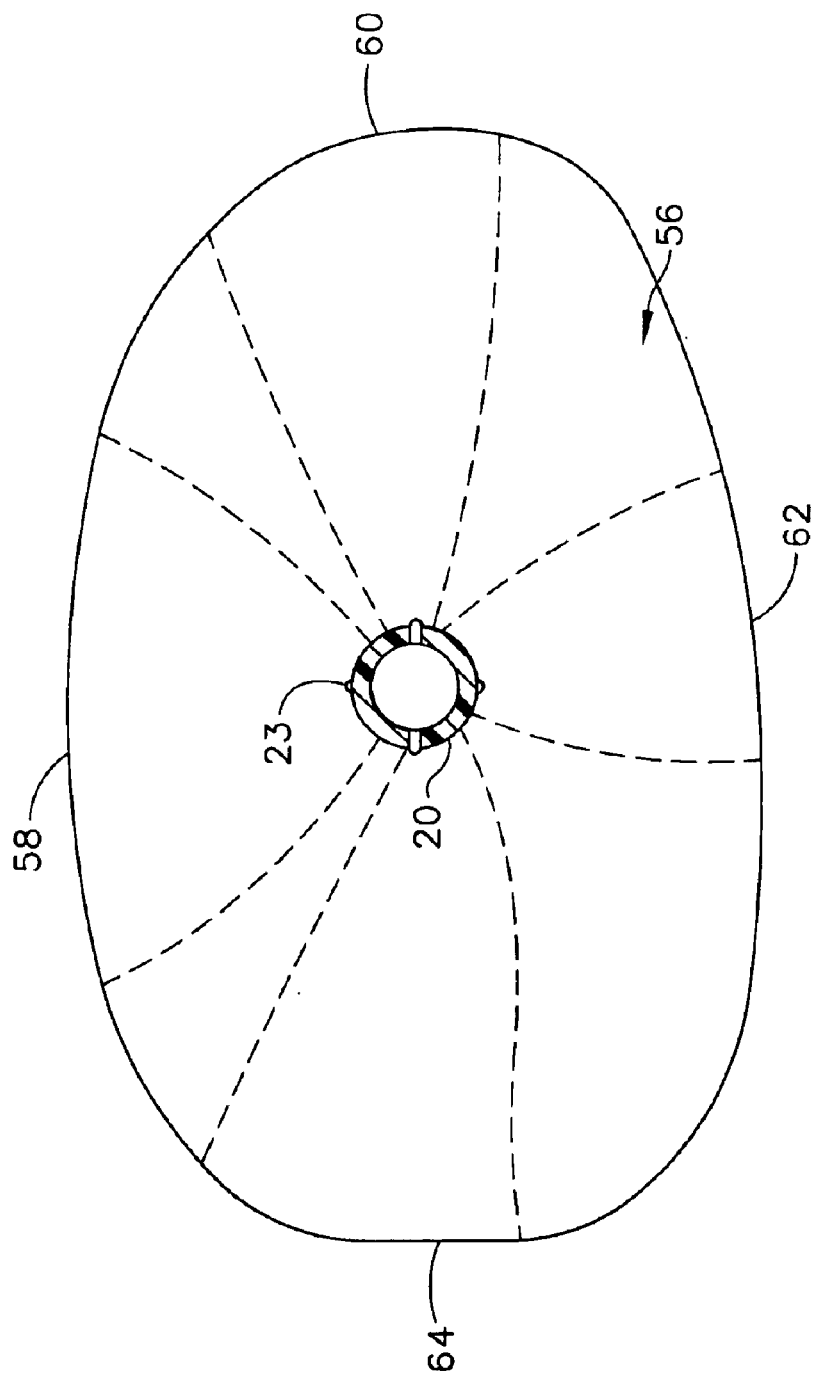
FIG. 5 shows a top plan section of a catheter of the invention in a heart chamber.

As shown in FIGS. 3A, 3B, 3C and 4, non-contact electrodes 25 and 25a in electrode arrays 23 and 23a are preferably discontinuous about the circumference of catheter distal ends 22 and 22a, respectively. FIG. 5 is a top plan section view of catheter 20 in heart chamber 56. Catheter 20 has its non-contact electrode array 23 arranged in four columns equally spaced about the catheter circumference. The discontinuous non-contact electrodes sense the electrical activity of distinct regions of the cardiac surface, designated as 58, 60, 62 and 64 in FIG. 5. In contrast, non-contact electrodes that are continuous about the catheter circumference would provide signals that would represent average electrical activity in the heart chamber, from which it would be more difficult to determine local electrical activity. Ring electrodes are an example of a continuous electrode geometry that completely encircles the catheter circumference, and, as such, are not preferred for use as the non-contact electrodes in the practice of the invention.

Additionally, it is important to note that the catheter 20 according to the present invention can optionally utilize the contact electrode 24 along with the non-contact electrode arrays 23 and 23a respectively. Accordingly, it is within the scope of the present invention to conduct a rapid diagnostic mapping procedure based on electrical information received through the non-contact electrodes 25 and 25a alone. While the catheter distal ends 22 and 22a shown in FIGS. 3A, 3B, 3C and 4 have bipolar distal tip contact electrodes, it will be understood that catheter distal ends containing unipolar distal tip electrodes are also considered to be within the scope of the present invention.

In practicing the method of the invention, it is necessary to know the position and orientation of each of the non-contact electrodes 25 and 25a contained in array 23 and 23a respectively of catheter 20. In order to know the location and orientation of each of the electrodes, the catheter of the invention used in the method of the invention preferably employs two or more location sensors such as sensors 28 and 48 as shown in FIG. 3C. One of these sensors is preferably placed in the catheter distal tip 26 while a second sensor is preferably placed at the proximal end 49 of the non-contact electrode array 23. Preferably, at least one of these location sensors provides six degrees of location and orientation information, i.e., three position coordinates (x, y and z) and the three orientation coordinates (pitch, roll and yaw). A suitable, location sensor 28 and 48 that provides six degrees of location information is described, for example in PCT application WO 96/05768, the disclosure of which is incorporated herein by reference.

Figure 6:
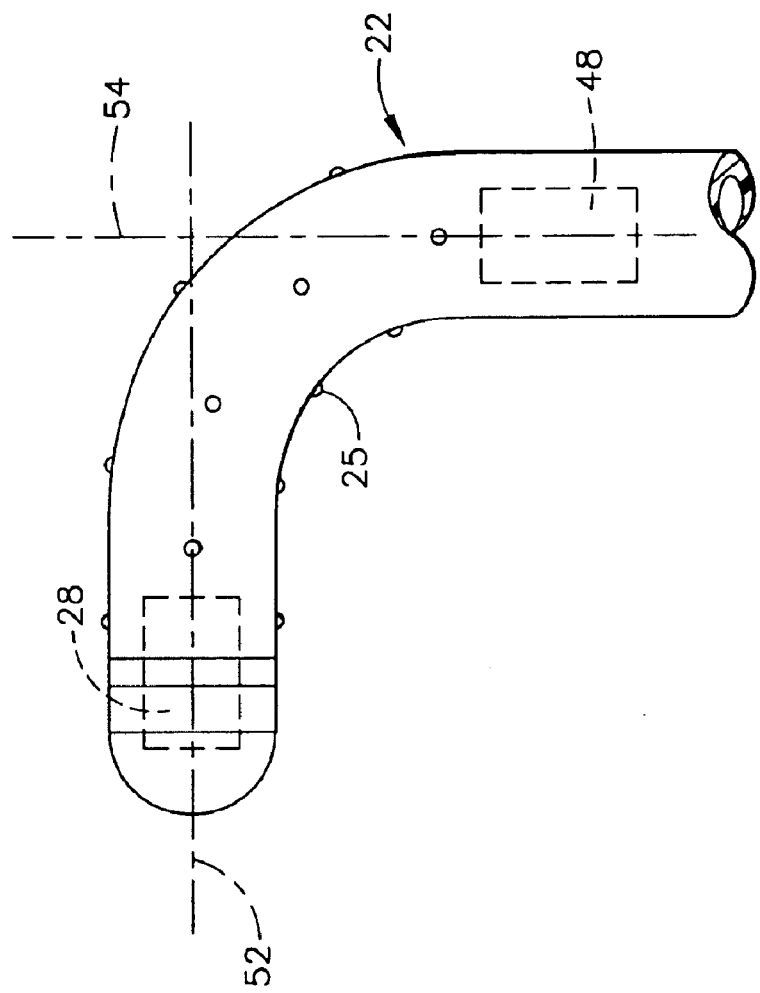
FIG. 6 shows the catheter of FIG. 3B in a deflected position.

FIG. 6 shows the catheter distal end 22 in FIG. 3B in a deflected position. The orientation of sensors 28 and 48 may be characterized by lines 52 and 54, which represent the axes passing through sensors 28 and 48, respectively. Knowing the three-dimensional position and orientation of each of the sensors and the geometry of the electrodes 25 at the catheter distal end 22, the position and orientation of each of the electrodes 25 may be calculated, for example, using spline techniques.

Under suitable circumstances, e.g., knowledge of the stiffness characteristics of the catheter, other image information, and the use of stiff, short non-contact electrode arrays, it may be possible to use a catheter having only a single position sensor in the practice of the method of the invention. In such cases, the sensor is preferably located at the catheter distal tip 26.

In catheters having multiple location sensors, not all sensors need to provide six degrees of location information. For example, as shown in FIG. 3C, sensor 28 preferably senses and transmits signals indicative of six degrees of location information. While sensor 48 may be a six-degree sensor, a sensor providing less than six degrees of location information may also be used. For example, a sensor which senses five degrees of location information (three position coordinates, pitch and yaw) is described in U.S. Pat. No. 5,913,820, the disclosure of which is incorporated herein by reference. Such sensors may be used as the second sensor proximate the proximate end 49 of electrode array 23. Alternatively, a plurality of location sensors, each providing less than six degrees of location information, may be used. For example, three or more location sensors, each providing three degrees of location information, may be used to define the location of all points on the catheter.

The catheter of the invention preferably has a diameter between about 5 French and about 11 French (3 French=1 mm). More preferably, the catheter of the invention has a diameter between about 6 French and about 8 French.

Another aspect of the present invention is directed to a method for rapidly generating an electrical map of a chamber 66 of the heart 29 that depicts an electrical characteristic of the chamber 66 as a function of chamber geometry within a brief time period. The method of the invention, as best illustrated in FIGS. 7A and 7B, includes advancing the catheter 20 into the chamber 66 of the heart 29. The contact electrode 24 at distal tip 26 of catheter 20 is then brought into contact with wall 68 of chamber 66 at first contact point 70. Contact electrode 24 is maintained in contact with wall 68 at contact point 70 throughout at least an entire cardiac cycle. During this time, location information, is continuously measured by location sensors 28 and 48, while electrical information, preferably, voltage (as a function of time), is measured by contact electrode 24 and each of the non-contact electrodes 25 in array 23.

After the above electrical and location information is collected at first contact point 70, contact electrode 24 at the catheter tip 26 is advanced to a second contact point on the chamber surface. FIG. 7B shows the contact electrode 24 in contact with second contact point 72 on chamber wall 68. FIG. 7B further shows point 70, the site of the first contact point, and points 74, shown as asterisks, which represent the location of the non-contact electrodes 25 while contact electrode 24 was at first contact point 70. Once again, contact electrode 24 is maintained in contact with wall 68 at contact point 72 throughout at least an entire cardiac cycle, during which time location information is measured by the location sensors, and electrical information is measured by contact electrode 24 and by each of the non-contact electrodes 25.

Contact electrode 24 is advanced over a plurality of contact points on the cardiac chamber surface, and location and electrical information is acquired while the contact electrode is in contact with each of the contact points. Preferably, the above-described contacting and information acquisition steps are effected at at least about five contact points on the cardiac chamber surface. More preferably, the contacting and information acquisition steps are effected at between about five and about fifteen contact points on the cardiac chamber surface. Assuming that data are acquired at ten contact points, it can be seen that using the catheter of FIGS. 3A–C for example, electrical data at a total of ten contact points and one hundred and sixty non-contact points (ten contact points×sixteen non-contact electrodes) would be available for the map generation step.

The resultant location and electrical information acquired at each of the above-defined process steps provides the starting point for generating an electrical map of the heart chamber.

There are two sources of location information useful in construction of the map of the cardiac chamber. The first source of information is the location of sensor 28 adjacent the catheter distal tip 26 at each of the contact points. The second source of information is the location of each of the non-contact electrodes while the contact electrode is in contact with each of the contact points.

The location of the contact electrodes at each of the contact points may be used to define the geometric map of the cardiac chamber. While not actually contacting the cardiac surface, the totality of the non-contact electrode locations defines a "cloud" of space which represents a minimum chamber volume. These non-contact locations may be used, alternatively, or together with the location of the contact electrodes at each of the contact points, to define the chamber geometry.

It is preferable to use a reference location sensor to correct for patient movement during the procedure or to movement of the heart due to patient breathing. One method of obtaining a location reference is by the use of a reference catheter containing a reference location sensor elsewhere in the heart. Alternatively, a reference location sensor may be contained in a pad that might be attached external to the patient, for example on the back of the patient. In either case, locations determined by the sensors contained in the mapping catheter may be corrected for patient movement with the reference sensors.

The method of the present invention may likewise use the known Rudy method, as previously described, to extract endocardial potentials from electrical measurements made by the non-contact electrode array. However, using the novel catheter 20 of the present invention in the novel manner disclosed herein, data taken by the contact electrode, which accurately measures endocardial potentials at the contact points, can be used to constrain the endocardial potentials determined from the non-contact electrodes. Furthermore, in contrast to the Rudy method where chamber geometry is determined independently, in the method of the invention, chamber geometry is determined by the location sensors simultaneous with the electrical measurements.

In the Beatty method, as described previously, expected endocardial potentials are computed based on measurements from the electrode array. The measured voltage at the surface-contacting reference electrode is used as a scaling factor in computation of the voltage map. The Beatty method may alternatively be used in the method of the present invention to generate local endocardial potentials from the combined contact and non-contact electrode measurements.

The resultant electrical potentials imputed to the cardiac surface by the non-contact electrode array can be used to reconstruct local endocardial electrograms. These reconstructed electrograms, together with the electrograms measured by contact electrode 24, provide the electrical information from which the electrical map of the heart chamber may be generated.

Alternatively, one can reconstruct a "virtual probe" which models the location and electrical information of the non-contact electrodes over all of the measurements, treating these as if they were acquired simultaneously in a single cardiac cycle. Electrical potentials at the virtual probe may be correlated with the surface of the heart wall in reconstructing the electrical map of the cardiac chamber.

A preferred electrical characteristic of the heart which may be mapped is the local activation time (LAT). LAT may be determined as a characteristic of the local electrograms, e.g., as the time associated with the maximum value of the local electrogram.

The local electrical characteristic that is mapped in the process of the invention is preferably referenced to a fiducial value. This value may, for example, be based on an electrical characteristic measured at a reference catheter elsewhere in the heart. Alternatively, the mapped electrical characteristic may be referenced to a particular feature of the body surface ECG signal.

A preferred method for generating the electrical map of the heart from the acquired location and electrical information is described in copending commonly assigned U.S. patent application Ser. No. 09/122,137 filed on Jul. 24, 1998, the disclosure of which is hereby incorporated in its entirety by reference. Briefly, in preferred embodiments of the present invention, a processor reconstructs a map, preferably a 3-D map, of the cardiac chamber from a plurality of sampled points on the chamber whose position coordinates have been determined. The processor is preferably capable of reconstructing the map based on a limited number of sampled points. Preferably, five to fifteen sampled points are sufficient in order to perform a preliminary reconstruction of the surface to a satisfactory quality.

An initial, generally arbitrary, closed 3-D curved surface (also referred to herein for brevity as a curve) is defined in a reconstruction space in the volume of the sampled points. The closed curve is roughly adjusted to a shape which resembles a reconstruction of the sampled points. Thereafter, a flexible matching stage is preferably repeatedly performed one or more times in order to bring the closed curve to accurately resemble the shape of the actual volume being reconstructed. Preferably, the 3D surface is rendered to a video display or other screen for viewing by a physician or other user of the map.

The initial closed curved surface preferably encompasses substantially all the sampled points or is interior to substantially all the sampled points. However, it is noted that any curve in the vicinity of the sampled points is suitable. Preferably, the closed 3D curved surface comprises an ellipsoid, or any other simple closed curve. Alternatively, a non-closed curve may be used, for example, when it is desired to reconstruct a single wall rather than the entire volume.

A grid of a desired density is defined on the curve. For each of the points on the grid, a vector is defined which is dependent on the displacement between one or more of the grid points and one or more of the measured locations on the cardiac surface. The surface is adjusted by moving each of the grid points in response to the respective vector, so that the reconstructed surface is deformed to resemble the actual configuration of the cardiac chamber. The grid preferably divides the curved surface into quadrilaterals or any other polygons such that the grid evenly defines points on the curve. Preferably, the grid density is sufficient such that there are generally more grid points than sampled points in any arbitrary vicinity. Further preferably, the grid density is adjustable according to a desired compromise between reconstruction accuracy and speed.

In preferred embodiments, dedicated graphics hardware, designed to manipulate polygons, is used to perform the reconstruction stages described above.

Preferably, after the geometric map of the chamber is constructed as described above, values of the electrical characteristic are determined for each of the grid points based on interpolation of the characteristic at surrounding points sampled by the contact electrode or imputed by the non-contact electrodes.

Thus, the method of the invention results in the generation of a map of an electrical characteristic of the heart chamber 66 as a function of chamber geometry. The electrical characteristic is preferably selected from local voltage, local impedance, local conduction velocity or local activation time.

Preferably, the electrical characteristic is displayed on the reconstructed surface based on a predefined color scale.

The method of the invention further preferably comprises outputting the generated map to a display device, preferably, a computer display or a computer printer.

The above-described method is especially useful to define the area of interest, i.e., that portion of the heart chamber which is responsible for irregular cardiac activity, to within a certain degree of accuracy. The accuracy of the map in the area of interest may be further refined by collecting additional electrical and positional contact information in that area.

In an alternative embodiment, the invention is directed to a method for generating an electrical map of a chamber of a heart wherein the map depicts an electrical characteristic of the chamber as a function of chamber geometry. In this method, the catheter 20 is advanced into the chamber 66 of the heart 29 as shown in FIGS. 7A and 7B wherein the wall 68 of the chamber 66 of the heart 29 is contacted with the catheter distal tip 26 at a plurality of contact points. Electrical information and location information from each of the electrodes and location sensors, respectively, is acquired. The acquisition takes place over at least one cardiac cycle while the catheter distal tip 26 is in contact with each of the contact points. An electrical map of the heart chamber is then generated from the acquired location and electrical information.

In this embodiment of the method of the present invention, the catheter 20 utilizes a first location sensor 28 and a second location sensor 48 as depicted in FIG. 3C. In this embodiment, the method of the invention may be effected even in the absence of a contact electrode 24 at the catheter distal tip 26 by deriving chamber locations from the location sensors 28 and 48, particularly from the location sensor 28 positioned at the catheter distal tip 26. The location of each of the non-contact electrodes are known from the location of the location sensors and the known geometry of the catheter. The chamber geometry may be defined and reconstructed as described above, and the electrical characteristic, derived from the non-contact electrodes, is mapped on the reconstruction as a function of chamber geometry.

The catheter, method and apparatus of the invention are directed to generating any of the maps commonly used by cardiologists. Exemplary mapping procedures that may be effected using the catheter, method and apparatus of the invention include sinus rhythm mapping, pace mapping and VT mapping.

Additionally, it is important to note that the contact electrode 24 at distal tip 26, in addition to mapping, is also useful to deliver therapy, such as RF energy ablation, through the contact electrode 24 at the distal tip 26 in order to ablate lesions at or near the endocardial surface. The catheter 20 of the invention is ideally suited to validate the effectiveness of the ablation procedure, preferably with the acquisition of the post-ablation electrical activity in a single cardiac beat.

It will be appreciated that the preferred embodiments described above are cited by way of example and the full scope of the invention is limited only by the claims which follow.

What is claimed is:

1. A catheter and console combination for mapping a chamber of a heart comprising:
   a console comprising driver circuits operatively connected to at least one electromagnetic field generator for generating an electromagnetic field, the console also comprising a signal processor for determining location information;
   a catheter comprising:
   (i) a body having a proximal end and a distal end, said distal end having a distal tip;
   (ii) a contact electrode at said distal tip;
   (iii) an array of non-contact electrodes on said distal end of said body, said array having a proximal end and a distal end, wherein said non-contact electrodes are linearly arranged along a longitudinal axis of said body; and
   at least one location sensor on said distal end of said body for generating signals in response to the electromagnetic field which is used by the signal processor to determine a location of said contact electrode and a location of said non-contact electrodes, the location of the non-contact electrodes determined by said signal processor from said signals generated by said at least one location sensor, said signal processor during at least an entire cardiac cycle in a first mode of operation acquiring first electrical information from only said non-contact electrodes, and in a second mode of operation acquiring second electrical information from said contact electrode and said non-contact electrodes to represent a minimum volume of the chamber geometry of the heart.

2. The catheter and console combination of claim 1 wherein said at least one location sensor is proximate to said catheter distal tip.

3. The catheter and console combination of claim 1 wherein said at least one location sensor comprises a first location sensor and a second location sensor, wherein said array of non-contact electrodes is disposed therebetween, and said second location sensor is disposed proximate to said catheter distal tip.

4. The catheter and console combination of claim 3 wherein at least one of said first location sensor and said second location sensor provides six degrees of location information.

5. The catheter and console combination of claim 4 wherein said first location sensor and said second location sensor each provide six degrees of location information.

6. The catheter and console combination of claim 3 wherein at least one of said first location sensor and said second location sensor is an electromagnetic location sensor.

7. The catheter and console combination of claim 1 wherein said distal tip contact electrode is a bipolar electrode.

8. The catheter and console combination of claim 1 wherein said electrode array comprises from about twelve to about thirty-two non-contact electrodes.

9. The catheter and console combination of claim 8 wherein said array comprises from about sixteen to about twenty-four electrodes.

10. The catheter and console combination of claim 3 wherein said distal tip contact electrode is a bipolar electrode.

11. A catheter and console combination comprising:
   (a) a console comprising driver circuits operatively connected to at least one electromagnetic field generator for generating an electromagnetic field, the console also comprising a signal processor for determining location information;
   (b) a catheter comprising:
   (i) a body having a proximal end and a distal end, said distal end having a distal tip;
   an array of non-contact electrodes on said distal end of said body, said array having a proximal end and a distal end;
   wherein said non-contact electrodes are linearly arranged along a longitudinal axis of said body; and
   at least one location sensor proximate to said distal tip for generating signals in response to the electromagnetic field which is used by the signal processor to determine a location of said non-contact electrodes, said at least one location sensor comprising a first location sensor and a second location sensor, said first location sensor being proximate to said catheter distal tip and said second location sensor being proximate to said proximal end of said non-contact electrode array, the location of said non-contact electrodes determined by said signal processor from said signals generated by said at least one location sensor, said signal processor using said location of the non-contact electrodes to represent a minimum volume of the chamber geometry of the heart; wherein said at least one location sensor provides six degrees of location information.

12. The catheter and console combination of claim 11 wherein at least one of said first location sensor and said second location sensor is an electromagnetic location sensor.

13. A method for generating an electrical map of a chamber of a heart, said map depicting an electrical characteristic of the chamber as a function of chamber geometry, said method comprising the steps of:
   providing a catheter comprising a body having a proximal end and a distal end, said distal end having a distal tip; a contact electrode at said distal tip; an array of non-contact electrodes on said distal end of said body, said array having a proximal end and a distal end, wherein said non-contact electrodes are linearly arranged along a longitudinal axis of said body; and at least one location sensor on said distal end of said body;
   advancing said catheter into said chamber of said heart;
   using a signal processor to determine a location of said contact electrode and a location of said non-contact electrodes using said at least one location sensor;
   contacting a wall of said chamber of said heart with said contact electrode at a plurality of contact points;
   acquiring electrical information and location information from each of said electrodes and said at least one location sensor, respectively, using the signal processor, said acquisition taking place over at least one cardiac cycle while said contact electrode is in contact with each of said contact points; said electrical information comprising first electrical information from said non-contact electrodes and second electrical information from said contact electrode and said non-contact electrodes;

determining a minimum volume of said heart chamber geometry with the signal processor during said at least one cardiac cycle in a first mode of operation by obtaining only said first electrical information from said non-contact electrodes, and in a second mode of operation by obtaining said second electrical information from said contact electrode and said non-contact electrodes; and generating an electrical map of said heart chamber from said acquired location and one of said first electrical information and said second electrical information.

14. The method of claim 13 wherein said at least one location sensor comprises a first location sensor and a second location sensor, wherein said array of non-contact electrodes is disposed therebetween, and said second location sensor is disposed proximate to said catheter distal tip.

15. The method of claim 14 wherein said second location sensor is proximate to the proximal end of said array of non-contact electrodes.

16. The method of claim 15 wherein at least one of said first location sensor and said second location sensor provides six degrees of location information.

17. The method of claim 16 wherein said first location sensor and said second location sensor each provide six degrees of location information.

18. The method of claim 14 wherein at least one of said location sensors is an electromagnetic location sensor.

19. The method of claim 13 wherein said contact electrode is a bipolar electrode.

20. The method of claim 13 wherein said array of non-contact electrodes comprises from about twelve to about thirty-two non-contact electrodes.

21. The method of claim 20 wherein said array of non-contact electrodes comprises from about sixteen to about twenty-four non-contact electrodes.

22. The method of claim 14 including determining said geometry of said heart chamber from the location information provided by of each of said location sensors.

23. The method of claim 13 wherein said generating step (e) comprises computing the location of said contact electrode and each of said non-contact electrodes, said locations being the location of said contact electrode and said non-contact electrodes during acquisition of said electrical and location information.

24. The method of claim 23 wherein said chamber geometry is derived from the location of said contact electrode and each of said non-contact electrodes during acquisition step (d).

25. The method of claim 24 wherein said electrical map is derived from:
(i) The location of said contact electrode and of each of said non-contact electrodes during acquisition of said electrical and location information; and from
(ii) The electrical information acquired by the contact electrode at each of said contact points.

26. The method of claim 25 wherein said electrical characteristics intermediate said contact points are derived from the electrical information acquired from said non-contact electrodes.

27. The method of claim 23 wherein said electrical map is derived from:
the location of said contact electrode and of each of said non-contact electrodes during acquisition of said electrical and location information; and from ii) The electrical information acquired by said contact electrode and each of said non-contact electrodes.

28. The method of claim 13, including ablating a portion of said heart chamber based on said electrical map.

29. The method of claim 28 which further comprises validating the effectiveness of the ablation procedure.

30. The method of claim 29 wherein said validation comprises acquiring additional electrical information from said catheter following said ablation procedure.

31. A method for generating an electrical map of a chamber of a heart, said map depicting an electrical characteristic of the chamber as a function of chamber geometry, said method comprising the steps of:

providing a catheter comprising a body having a proximal end and a distal end, said distal end having a distal tip; an array of non-contact electrodes on said distal end of said body, said array having a proximal end and a distal end, wherein said non-contact electrodes are linearly arranged along a longitudinal axis of said body; and at least one location sensor proximate to said catheter distal tip;

advancing said catheter into said chamber of said heart;

using a signal processor to determine a location of said non-contact electrodes using said at least one location sensor;

contacting a wall of said chamber of said heart with said catheter distal tip at a plurality of contact points;

acquiring electrical information and location information from each of said non-contact electrodes and said at least one location sensor, respectively, using the signal processor, said acquisition taking place over at least one cardiac cycle while said catheter distal tip is in contact with each of said contact points;

determining a minimum volume of said heart chamber geometry with the signal processor using the location of the non-contact electrodes; and generating an electrical map of said heart chamber from said acquired location and electrical information; wherein said at least one location sensor provides six degrees of location information; and wherein said at least one location sensor comprises a first location sensor and a second location sensor, and said array of non-contact electrodes is disposed therebetween.

32. The method of claim 31 including ablating a portion of said heart chamber based on said electrical map.

33. The method of claim 32 which further comprises validating the effectiveness of the ablation procedure.

34. The method of claim 33 wherein said validation comprises acquiring additional electrical information from said catheter following said ablation procedure.

35. Apparatus for generating an electrical map of a chamber of a heart, said map depicting an electrical characteristic of the chamber as a function of chamber geometry, said apparatus comprising:

a console comprising driver circuits operatively connected to at least one electromagnetic field generator for generating an electromagnetic field, the console also comprising a signal processor for determining location information;

a catheter comprising:

a body having a proximal end and a distal end, said distal end having a distal tip; a contact electrode at said distal tip;

an array of non-contact electrodes on said distal end of said body, said array having a proximal end and a distal end, wherein said non-contact electrodes are linearly arranged along a longitudinal axis of said body; and at least one location sensor on said distal end of said body for generating signals in response to the electromagnetic field which is used by said signal processor to determine a location of said contact electrode and a location of said non-contact electrodes, the location of the non-contact electrodes determined by said signal processor from said signals generated by said at least one location sensor, said signal processor using said location of the non-contact electrodes to represent a minimum volume of the chamber geometry of the heart; said catheter being adapted to contacting a wall of said chamber of said heart with said contact electrode at a plurality of contact points; said signal processor operatively connected to said catheter for acquiring location information from said-location sensors, and in a first mode of operation acquiring first electrical information only from said non-contact electrodes, and in a second mode of operation acquiring second electrical information from said contact electrode and said non-contact electrodes, over at least one cardiac cycle while said contact electrode is in contact with each of said contact points, said signal processor also generating an electrical map of said heart chamber from said acquired location information and one of said first electrical information and said second electrical information.

36. The apparatus of claim 35 wherein said catheter comprises a first location sensor and a second location sensor.

37. The apparatus of claim 36 wherein at least one of said first location sensor and said second location sensor is an electromagnetic location sensor.

38. The apparatus of claim 36 wherein said first location sensor is proximate to said catheter distal tip.

39. The apparatus of claim 38 wherein said second location sensor is proximate to the proximal end of said electrode array.

40. Apparatus for generating an electrical map of a chamber of a heart, said map depicting an electrical characteristic of the chamber as a function of chamber geometry, said apparatus comprising:

(a) console comprising driver circuits operatively connected to at least one electromagnetic field generator for generating an electromagnetic field, the console also comprising a signal processor for determining location information;

(b) catheter comprising:

a catheter including a body having a proximal end and a distal end, said distal end having a distal tip; an array of non-contact electrodes on said distal end of said body, said array having a proximal end and a distal end, wherein said non-contact electrodes are linearly arranged along a longitudinal axis of said body; and at least one location sensor proximate to said catheter distal tip for generating signals in response to the electromagnetic field which is used by the signal processor to determine a location of said non-contact electrodes, said at least one location sensor comprising a first location sensor and a second location sensor, wherein said array of non-contact electrodes is disposed therebetween, and said second location sensor is disposed proximate to said catheter distal tip, the location of said non-contact electrodes determined by said signal processor for said signals generated by said at least one location sensor, said signal processor using said location of said non-contact electrodes to represent a minimum volume of the chamber geometry of the heart; said catheter being adapted to contacting a wall of said chamber of said heart with said catheter distal tip at a plurality of contact points;

said signal processor acquiring electrical information and location information from each of said electrodes and location sensors, respectively, over at least one cardiac cycle while said catheter distal tip is in contact with each of said contact points; said signal processor also generating an electrical map of said heart chamber from said acquired location and electrical information, wherein said at least, one location sensor provides six degrees of location information.

41. The apparatus of claim 40 wherein at least one of said first location sensor and said second location sensor is an electromagnetic location sensor.

* * * * *